United States Patent
Wang et al.

(10) Patent No.: US 10,220,062 B2
(45) Date of Patent: Mar. 5, 2019

(54) METHOD OF PREPARING MIRABILITUM PRAEPARATUM BY PURE STRAIN FERMENTATION AND ITS APPLICATIONS

(71) Applicants: Qiuhong Wang, Guangzhou, Guangdong (CN); Haixue Kuang, Guangzhou, Guangdong (CN)

(72) Inventors: Qiuhong Wang, Guangzhou (CN); Haixue Kuang, Guangzhou (CN); Changfu Wang, Guangzhou (CN); Zunpeng Shu, Guangzhou (CN); Na Xing, Guangzhou (CN)

(73) Assignees: Qiuhong Wang, Daxue (CN); Haixue Kuang, Daxue (CN)

( * ) Notice: Subject to any disclaimer, the term of this patent is extended or adjusted under 35 U.S.C. 154(b) by 11 days.

(21) Appl. No.: 15/356,430

(22) Filed: Nov. 18, 2016

(65) Prior Publication Data

US 2017/0326187 A1    Nov. 16, 2017

(30) Foreign Application Priority Data

May 10, 2016    (CN) .......................... 2016 1 0308972

(51) Int. Cl.

| | |
|---|---|
| *A61K 36/42* | (2006.01) |
| *A61K 36/062* | (2006.01) |
| *A61K 9/00* | (2006.01) |
| *A61K 9/20* | (2006.01) |
| *A61K 9/70* | (2006.01) |
| *A61Q 11/00* | (2006.01) |
| *A61Q 19/00* | (2006.01) |
| *A61K 8/9728* | (2017.01) |

(52) U.S. Cl.
CPC .......... *A61K 36/062* (2013.01); *A61K 8/9728* (2017.08); *A61K 9/006* (2013.01); *A61K 9/0053* (2013.01); *A61K 9/20* (2013.01); *A61K 9/2059* (2013.01); *A61K 9/70* (2013.01); *A61Q 11/00* (2013.01); *A61Q 19/00* (2013.01); *A61K 2236/00* (2013.01); *A61K 2800/80* (2013.01)

(58) Field of Classification Search
None
See application file for complete search history.

(56) References Cited

FOREIGN PATENT DOCUMENTS

CN    103550282 A  *  2/2004

OTHER PUBLICATIONS

Laarhoven K. et al. A Microscopy Study of Hyphal Growth of Penicillium rubens on Gypsum Under Dynamic Humidity Conditions. Microbial Biotechnology 9(3)408-418, 2016. (Year: 2016).*

* cited by examiner

*Primary Examiner* — Ralph J Gitomer
(74) *Attorney, Agent, or Firm* — Schwabe Williamson & Wyatt, PC

(57) ABSTRACT

The present invention involves a method of preparing Mirabilitum Praeparatum by pure strain fermentation and its application in treating infectious and inflammatory diseases, as well as health products and cosmetics. The method involves blending the ripe fruit (watermelon) of *Citrullus lanatus* (Thunb.) Matsum. et Nakai with mirabilitum ($Na_2SO_4 \cdot 10H_2O$) according to a certain ratio as culture media and the pure strain *Penicillium rubens* as zymocyte, and then fermenting under a certain temperature. The Mirabilitum Praeparatum prepared by present method is different from that of prepared by traditional technology significantly, and the present invention possesses more advantages than the traditional method. The Mirabilitum Praeparatum prepared by present method, its extract shows powerful antibacterial and anti-inflammatory activities, which can be prepared into pharmaceutical preparations to treat infectious diseases of mucous membrane and skin, such as cavum oris ulcer, paradentosis, glossitis, rhinitis, laryngopharyngitis, dermatitis, otitis media, uterine cervicitis, kysthitis, and other health products and cosmetics.

5 Claims, 1 Drawing Sheet

Specification includes a Sequence Listing.

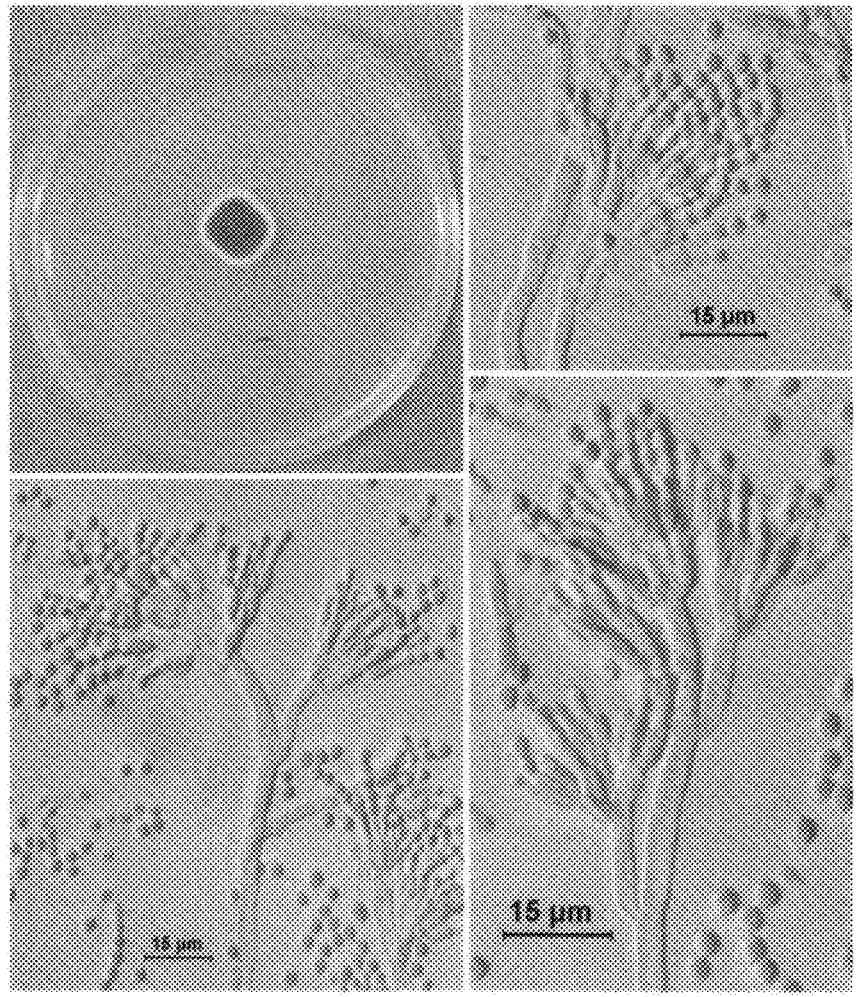

Fig. 1

Seq. ID No. 1

5'-AAGTCGTAACAAGGTTTCCGTAGGTGAACCTGCGGAAGGATCATTACCGAGTGAGGGCCCTCTGGGTC
CAACCTCCCACCCGTGTTTATTTTACCTTGTTGCTTCGGCGGGCCCGCCTTAACTGGCCGCCGGGGGCTT
ACGCCCCGGGCCCGCGCCCGCCGAAGACACCCTCGAACTCTGTCTGAAGATTGTAGTCTGAGTGAAAATA
TAAATTATTTAAAACTTTCAACAACGGATCTCTTGGTTCCGGCATCGATGAAGAACGCAGCGAAATGCGAT
ACGTAATGTGAATTGCAAATTCAGTGAATCATCGAGTCTTTGAACGCACATTGCGCCCCCTGGTATTCCGG
GGGGCATGCCTGTCCGAGCGTCATTTCTGCCCTCAAGCACGGCTTGTGTGTTGGGCCCCGTCCTCCGATCC
CGGGGGACGGGCCCGAAAGGCAGCGGCGGCACCGCGTCCGGTCCTCGAGCGTATGGGGCTTTGTCACCCGC
TCTGTAGGCCCGGCCGGCGCTTGCCGATCAACCCAAATTTTTATCCAGGTTGACCTCGGATCAGGTAGGGT
A -3'

Fig. 2

METHOD OF PREPARING MIRABILITUM PRAEPARATUM BY PURE STRAIN FERMENTATION AND ITS APPLICATIONS

CROSS REFERENCE OF RELATED APPLICATIONS

The present application claims the priority of Chinese Patent Application No. 201610308972.6, as filed on May 10, 2016 and titled with "A method of preparing Mirabilitum Praeparatum by pure strain fermentation and its applications", and the disclosure of which is incorporated herein by reference.

FIELD

The present invention involves in fields of bioengineering and Chinese medicinal materials production, especially involves in a pure strain fermentation method of preparing Mirabilitum Praeparatum by *Penicillium rubens*.

BACKGROUND

As a traditional Chinese medicine, Mirabilitum Citrulli Preparatum (referred to herein as "Mirabilitum Praeparatum") is a white amorphous powder made by processing the fresh ripe fruit (watermelon) of *Citrullus Ianatus* (Thunb.) Matsum. et Nakai with Mirabilitum (also known as "Glauber's salt"). The traditional preparation method of Mirabilitum Praeparatum was as following: the ripe fruit (watermelon) of *Citrullus Ianatus* (Thunb.) Matsum. et Nakai was cut off a thick slice along the pedicel as top cover, remove some pulp to add some Mirabilitum, and then recover the top cover and fix with bamboo stick. After that, watermelon was put into an earthen pot and covered, and then locate the earthen pot at a shady and cool place with ventilate, waiting for the hoar frost precipitating from the watermelon and collecting as soon as possible until no hoar frost precipitated.

Mirabilitum Praeparatum with potencies of clearing away the heat evil and expelling superficial evils and detumescence and analgetic, has a long history in treating sore throat, pharyngitis, and aphtha. Mirabilitum Praeparatum which is called "panacea of laryngology", has been considered as a miracle pharmaceutical preparation to cure diseases of throat and cavum oris by doctors of successive dynasties in China. In traditional Chinese medicine theories, potencies of clearing away the heat evil and expelling superficial evils and detumescence and analgetic for Mirabilitum Praeparatum lie in the ripe fruit (watermelon) of *Citrullus Ianatus* (Thunb.) Matsum. et Nakai with potency of clearing away summer-heat and Mirabilitum with potency of clearing away heat and reducing fire, processed the watermelon with Mirabilitum will improve the potency synergetic. At present, studies on Mirabilitum Praeparatum focus on the clinical observations and new applications. More compounds of Mirabilitum Praeparatum have been used in clinical, such as Guilin Xiguashuang spray, Xiguashuang lozenge, Xiguashuang buccal tablets, and Guilin Xiguashuang capsules.

The traditional preparations of Mirabilitum Praeparatum were various all over the country. The inconformity and miscellaneous in preparation technology, serious pollution such as the pathogenic bacteria in production, too long production cycle, inefficiency, unclear mechanism, and instability quality for Mirabilitum Praeparatum was not suitable for the modern production. Consequently, most Mirabilitum Praeparatum production factories were forced to shut down successively in 1970s.

In previous study, we found that the traditional preparation of Mirabilitum Praeparatum was actually a fermental process and the secondary metabolites from microorganisms were the therapeutic basis of Mirabilitum Praeparatum. This is different from the traditional viewpoint that considered the mirabilitum and amine acid from the ripe fruit (watermelon) of *Citrullus Ianatus* (Thunb.) Matsum. et Nakai as the therapeutic basis of Mirabilitum Praeparatum. Therefore, the present invention will prepare Mirabilitum Praeparatum by fermental method. The optimized fermental technology was obtained by determining the natural strain participated in the fermental process of Mirabilitum Praeparatum. As a result, the produced Mirabilitum Praeparatum possessed short production cycle, stable quality and no pollution. In addition, present invention also confirmed that the obtained Mirabilitum Praeparatum could exert its therapeutic effects through inhibiting and killing the common pathogenic bacteria that cause sore throats and mouth and tongue dermatitis by experiment. The Mirabilitum Praeparatum extract prepared in present invention can be prepared into pharmaceutical preparation to treat infectious diseases of mucous membrane and skin, such as cavum oris ulcer, paradentosis, glossitis, rhinitis, laryngopharyngitis, dermatitis, otitis media, uterine cervicitis, kysthitis, and other health products and cosmetics.

SUMMARY

To accomplish the objective mentioned above, the present invention provided a strain of *Penicillium rubens* for the pure strain fermentation of Mirabilitum Praeparatum. The *Penicillium rubens* was obtained as the following method: The plate streak and Purification of mycelium methods were used to separate a fungi from Mirabilitum Praeparatum fermented with traditional method. The strain was identified by Institute of Microbiology, Chinese Academy of Sciences and provided report [(2016) Micro discrimination, 032], and the strain was determined as *Penicillium rubens*. The colonial morphology and microscopic identifications of *Penicillium rubens* are shown in manual drawings of FIG. 1, while molecular biology identification is shown in FIG. 2.

On the one hand, the present invention provided a pure strain fermental method to prepare Mirabilitum Praeparatum with *Penicillium rubens* described above and the detail procedure as following:

The fresh ripe fruit (watermelon) of *Citrullus Ianatus* (Thunb.) Matsum. et Nakai is cut into small pieces and put into fermenter, and then adds mirabilitum according the ratio of 100:50-100:1 (watermelon/mirabilitum, m/m) to mix homogeneously. The mixture is sterilized with high-pressure steam for 20 min at 121° C., and inoculate pure strain of *Penicillium rubens* to ferment for 10-20 d at 19-27° C., dissolving oxygen during fermentation. After that, the mixture is centrifugated for 10-20 min at the speed of 4000 r/min and the obtained supernate is dried with freezer dryer (−40° C., <13 Pa) to obtain the Mirabilitum Praeparatum.

In one optimized implementation example of the present invention, the zymophyte is *Penicillium rubens*.

In one optimized implementation example of the present invention, the described ratio of the ripe fruit (watermelon) of *Citrullus Ianatus* (Thunb.) Matsum. et Nakai and mirabilitum (m/m) is 100:50-100:1, and the optimized ratio is 20:3.

In the other optimized implementation example of the present invention, the described fermental temperature is 19-27° C., and the optimized temperature is 25° C.

In the other optimized implementation example of the present invention, the described fermental period is 15-35 d, at least 15 d.

On the other hand, the present invention provided the application of Mirabilitum Praeparatum prepared with pure strain fermentation in preparing pharmaceutical preparations to infectious diseases. The Mirabilitum Praeparatum prepared with pure strain fermentation is cold-soak extracted with 95% ethanol for 2-4 times at 20-25° C., stir thoroughly and filter. The filtrate is dried at 40-50° C. under reduced pressure to obtain the extract of Mirabilitum Praeparatum. The extract is added acceptable excipients of pharmaceutical preparations, health care products and cosmetics to prepare any suitable products according to routine methods.

In one optimized implementation example of the present invention, the described infectious diseases of mucous membrane and skin include cavum oris ulcer, paradentosis, glossitis, rhinitis, laryngopharyngitis, dermatitis, otitis media, uterine cervicitis, kysthitis, respectively.

In the other optimized implementation example of the present invention, the product format of described pharmaceutical preparations, health care products and cosmetics are oral gel, membranae, unguentum, tincture, aerosols, dry powder inhalation, and ear drops.

The present invention optimized the fermental materials ratio, fermental temperature, and fermental time, determining the optimum technology parameter to prepare and obtain the Mirabilitum Praeparatum. Extracted the Mirabilitum Praeparatum and studied on the activity of the extract by antibacterial experiment in vitro, the results showed that Mirabilitum Praeparatum extract inhibit and kill the common pathogenic bacteria, such as *Aeruginosus bacillus, Staphylococcus aureus, Staphylococcus citreus, Staplylococcus albus, Aeruginosus bacillus, Bacillus paratyphosus B, Beta-hemolytic streptococci, Shigella flexneri,* and *Escherichia coli* significantly. Therefore, the extract is the effective fraction of Mirabilitum Praeparatum.

DESCRIPTION OF THE DRAWINGS

FIG. 1 is the fermental strain colonial morphology of Mirabilitum Praeparatum and the microscopic identification of the strain.

FIG. 2 is molecular biological assay of the Mirabilitum Praeparatum fermental strain, i.e., the results of rRNA gene sequences assay (SEQ. ID NO. 1).

DETAILED DESCRIPTION

The technical solution of the present invention will be detailed introduced by the implementation method below. It should be pointed out that the following instructions just are some examples of protected technical solutions not the limitations to the technical solutions, and the protective range will take the CLAIMS of the present invention as valid.

Example 1: The Separation and Purification of Mirabilitum Praeparatum Fermental Strain (*Penicillium rubens*)

1. The fresh ripe fruit (watermelon) of *Citrullus Ianatus* (Thunb.) Matsum. et Nakai was cut into small pieces and put into fermenter, and then added 15% mirabilitum (mirabilitum/watermelon, m/m) to mix homogeneously. The mixture was fermented at room temperature for 15 d, and then took 10 mL fermentation broth into 250 mL conical flask with 90 mL sterile water and small glass beads. After that, the solution was oscillated on swing bed for 20 min to scatter the microorganic cells, standing for 20 s-30 s and the 10:1 dilution was obtained. The dilution was further diluted into the concentration of $10^{-2}$-$10^{-9}$ successively for standby. The spread plate method was used to separate the strains and 0.2 mL of each solution was spread on plates with cultures of PDA, CZA, Sabourand and beef-protein medium respectively. The plates with PDA, CZA, Sabourand were cultured in incubator at 25° C., while the plate with beef-protein medium was cultured in incubator at 37° C. Take single colonies from plates for pure strain culture.

2. Take the inner and outer surface fermentation broth with Inoculation loops spread on plates with cultures of PDA, CZA, Sabourand and beef-protein medium respectively (once a day). The plates with PDA, CZA, Sabourand were cultured in incubator at 25° C., while the plate with beef-protein medium was cultured in incubator at 37° C. Take single colonies from plates for pure strain culture.

3. Observed the plate medium every day for monitoring the mycelium grown or single colonies forming, and picking the promycelium or single colonies to inoculate on sterile plate mediums as soon as possible. When the fungus colonies appeared, the single colonies were separated and inoculated on sterile plate mediums for purification according to the differences of colonial morphology, colonial colour, and the time of outgrow. The purified strain was inoculate on PDA or beef-protein slant culture-medium and numbered to storage in refrigerator at 4° C.

4. The results: a fungus was separated from the fermentation broth of Mirabilitum Praeparatum, and identified as *Penicillium* by its morphology.

5. The colonial morphology, microscopic, and Molecular Biology identifications of Mirabilitum Praeparatum fermental strain.

Morphology and microscopic identifications: the strain grew slow in Malt Extract Agar (MEA), cultured away from light for 5 d at 25° C. and the diameter of the colony was up to 15-17 mm, velvet in texture, producing much conidial fructification, conidial powder was pewter, the back of the colony was sandy beige, no hydrophilic pigment, the conidiophore was not specialization obviously, 3.0-5.0 μm in breadth, cytoderm was smoothly, 2~4 whorl penicillus and surface loosening, the phialide was 7.4~13.9×2.6~3.4 μm, conidiospore was subsphaeroidal and broad ellipse, reseda, smooth surface, 3.0-5.0×2.5-4.0 μm, and there was no sexual spore. (See the FIG. 1).

The identification of the strain was commissioned to Institute of Microbiology, Chinese Academy of Sciences and the report [(2016) Micro discrimination, 032] was issued. The genes of the strain contains the 18S rRNA fragment, ITS1、5.8S rRNA, ITS2, and 28S rRNA fragment sequences. Therefore, the strain was identified as *Penicillium rubens* (See the FIG. 2).

Example 2: Pure Strain Fermentation Prepared Mirabilitum Praeparatum in Various Proportions of Fermental Materials The fresh ripe fruit (watermelon) of *Citrullus Ianatus* (Thunb.) Matsum. et Nakai is cut into small pieces and put into fermenter, and then adds mirabilitum according the ratio of 2:1, 10:3, 5:1, 20:3, 10:1, and 20:1 respectively (watermelon/mirabilitum, m/m) to mix homogeneously. The mixture is sterilized with high-pressure (15 psi) steam for 20 min at 121° C., and inoculate pure strain of *Penicillium rubens* to ferment for 15 d at 25° C., dissolving oxygen during fermentation. After that, the mixture is centrifugated for 10-20 min at the speed of 4000 r/min and the obtained supernate is dried with freezer dryer (−40° C., <13 Pa) to obtain the Mirabilitum Praeparatum.

TABLE 1

The antibacterial activities (minimum inhibitory concentration, MIC) of pure strain fermentation prepared Mirabilitum Praeparatum in various proportions of fermental materials (watermelon/mirabilite, m/m)

| | (MIC, mg/mL) | | | | | |
|---|---|---|---|---|---|---|
| Strains | 2:1 | 10:3 | 5:1 | 20:3 | 10:1 | 20:1 |
| Aeruginosus bacillus | — | 12.53 | 3.13 | 3.13 | 6.26 | 25.06 |
| Escherichia coli | — | 6.26 | 3.13 | 3.13 | 3.13 | 25.06 |
| Staplylococcus albus | — | 12.53 | 3.13 | 3.13 | 3.13 | 25.06 |
| Staphylococcus citreus | — | 12.53 | 3.13 | 3.13 | 3.13 | 25.06 |
| Shigella flexneri | — | 12.53 | 3.13 | 3.13 | 6.26 | 25.06 |
| Staphylococcus aureus | — | 12.53 | 6.26 | 3.13 | 6.26 | 25.06 |
| Bacillus paratyphosus B | — | 12.53 | 3.13 | 3.13 | 6.26 | 25.06 |
| Beta-hemolytic streptococci | — | 12.53 | 3.13 | 3.13 | 6.26 | 25.06 |

Example 3: Pure Strain Fermentation Prepared Mirabilitum Praeparatum in Various Temperatures The fresh ripe fruit (watermelon) of *Citrullus Ianatus* (Thunb.) Matsum. et Nakai is cut into small pieces and put into fermenter, and then adds mirabilitum according the ratio of 20:3 (watermelon/mirabilitum, m/m) to mix homogeneously. The mixture is sterilized with high-pressure (15 psi) steam for 20 min at 121° C., and inoculate pure strain of *Penicillium rubens* to ferment for 15 d at 21° C., 23° C., 25° C., 27° C., and 31° C. respectively, dissolving oxygen during fermentation. After that, the mixture is centrifugated for 10-20 min at the speed of 4000 r/min and the obtained supernate is dried with freezer dryer (−40° C., <13 Pa) to obtain the Mirabilitum Praeparatum.

TABLE 2

The antibacterial activities of pure strain fermentation prepared Mirabilitum Praeparatum in various temperatures

| | (MIC, mg/mL) | | | | | |
|---|---|---|---|---|---|---|
| Strains | 19° C. | 22° C. | 25° C. | 28° C. | 31° C. | 33° C. |
| Aeruginosus bacillus | 6.26 | 6.26 | 3.13 | 12.53 | 50.12 | 50.12 |
| Escherichia coli | 6.26 | 6.26 | 3.13 | 12.53 | 50.12 | 50.12 |
| Staplylococcus albus | 6.26 | 6.26 | 3.13 | 12.53 | 50.12 | 50.12 |
| Staphylococcus citreus | 6.26 | 6.26 | 3.13 | 12.53 | 50.12 | 50.12 |
| Shigella flexneri | 6.26 | 6.26 | 3.13 | 12.53 | 50.12 | 50.12 |
| Staphylococcus aureus | 6.26 | 6.26 | 3.13 | 12.53 | 50.12 | 50.12 |
| Bacillus paratyphosus B | 6.26 | 6.26 | 3.13 | 12.53 | 50.12 | 50.12 |
| Beta-hemolytic streptococci | 6.26 | 6.26 | 3.13 | 12.53 | 50.12 | 50.12 |

Example 4: Pure Strain Fermentation Prepared Mirabilitum Praeparatum in Various Fermental Times The fresh ripe fruit (watermelon) of *Citrullus Ianatus* (Thunb.) Matsum et Nakai is cut into small pieces and put into fermenter, and then adds mirabilitum according the ratio of 20:3 (watermelon/mirabilitum, m/m) to mix homogeneously. The mixture is sterilized with high-pressure (15 psi) steam for 20 min at 121° C., and inoculate pure strain of *Penicillium rubens* to ferment for 3 d, 7d, 10 d, 15 d, 20 d, 25 d, and 30 d respectively at 25° C., dissolving oxygen during fermentation. After that, the mixture is centrifugated for 10-20 min at the speed of 4000 r/min and the obtained supernate is dried with freezer dryer (−40° C., <13 Pa) to obtain the Mirabilitum Praeparatum.

TABLE 3

The antibacterial activities of pure strain fermentation prepared Mirabilitum Praeparatum in various fermental periods

| | (MIC, mg/mL) | | | | | | |
|---|---|---|---|---|---|---|---|
| Strains | 3 d | 7 d | 10 d | 15 d | 20 d | 25 d | 30 d |
| Aeruginosus bacillus | 50.12 | 12.53 | 6.26 | 3.13 | 3.13 | 3.13 | 12.53 |
| Escherichia coli | 50.12 | 12.53 | 6.26 | 3.13 | 3.13 | 3.13 | 12.53 |
| Staplylococcus albus | 50.12 | 12.53 | 6.26 | 3.13 | 3.13 | 3.13 | 12.53 |
| Staphylococcus citreus | 50.12 | 12.53 | 6.26 | 3.13 | 3.13 | 3.13 | 12.53 |
| Shigella flexneri | 50.12 | 12.53 | 6.26 | 3.13 | 3.13 | 3.13 | 12.53 |
| Staphylococcus aureus | 50.12 | 12.53 | 6.26 | 3.13 | 3.13 | 3.13 | 12.53 |
| Bacillus paratyphosus B | 50.12 | 12.53 | 6.26 | 3.13 | 3.13 | 3.13 | 12.53 |
| Beta-hemolytic streptococci | 50.12 | 12.53 | 6.26 | 3.13 | 3.13 | 3.13 | 12.53 |

Example 5: Determination of the Optimized Preparation Technology of Mirabilitum Praeparatum The Examples 2-4 about Mirabilitum Praeparatum showed that the optimized ratio of the ripe fruit (watermelon) of *Citrullus Ianatus* (Thunb.) Matsum et Nakai and mirabilitum was 20:3 (m/m), the optimized fermental temperature was 25° C., and the optimized fermental time was 15-17 d. As a result, the optimized preparation technology of Mirabilitum Praeparatum was determined as following: The fresh watermelon is cut into small pieces and put into fermenter, and then adds mirabilitum according the ratio of 20:3 (watermelon/mirabilitum, m/m) to mix homogeneously. The mixture is sterilized with high-pressure (15 psi) steam for 20 min at 121° C., and inoculate pure strain of *Penicillium rubens* to ferment for at least 15 d at 25° C., dissolving oxygen during fermentation. After that, the mixture is centrifugated for 10-20 min at the speed of 4000 r/min and the obtained supernate is dried with freezer dryer (−40° C., <13 Pa) to obtain the Mirabilitum Praeparatum.

Example 6: The Antibacterial Test of Mirabilitum Praeparatum In Vitro

The Mirabilitum Praeparatum prepared in Example 5 was lixiviated 3 times with 95% ethanol of 8 times amount (v/m) at 20° C. The extracted liquid was retrieved ethanol under reduce pressure after filtered the undissolved $Na_2SO_4$ to obtained Mirabilitum Praeparatum extract. The antibacterial test in vitro was used to investigate the activities of. The selected bacterial strains are common pathogenic bacteria of cavum oris, respiratory tract and digestive tract, such as *Aeruginosus bacillus, Staphylococcus aureus, Staphylococcus citreus, Staplylococcus albus, Aeruginosus bacillus, Bacillus paratyphosus* B, Beta-hemolytic streptococci, *Shigella flexneri*, and *Escherichia coli*.

Determination of MICs: On a 96-well microplate, the first one in each row (12 wells) was added 100 μL broth culture with Mirabilitum Praeparatum extract, while the remaining 11 wells were added with 100 μL broth culture for serial dilution. Another 100 μL each solution was added into the second well and then 100 μL was sequentially transferred to the next wells till the tenth well. The last two wells served as growth control and sterility check. And then 100 jut of inoculum was added into all the wells except the last one in which 100 μL broth instead. The microplate was incubated at 37° C. for 18 h and a microplate reader was used to monitor the growth of the bacterial strains. The parallel experiment was tested for 3 times and the result was showed in table 4.

TABLE 4

The antibacterial activities of pure strain fermentation
prepared Mirabilitum Praeparatum extract

| Strains | (MIC, mg/mL) |
|---|---|
| Aeruginosus bacillus | 3.13 |
| Escherichia coli | 3.13 |
| Staplylococcus albus | 3.13 |
| Staphylococcus citreus | 3.13 |
| Shigella flexneri | 3.13 |
| Staphylococcus aureus | 3.13 |
| Bacillus paratyphosus B | 3.13 |
| Beta-hemolytic streptococci | 3.13 |

Example 7: Mirabilitum Praeparatum Cavum Oris Gelata

Carbomer gelatin matrix was weighted and put into mortar, added glycerol and grinded to moist. After that, the mixture was added triethanolamine and grinded into transparent gelatin matrix. An appropriate amount of Mirabilitum Praeparatum extract and ethylparaben was weighted added purified water and heated to dissolve. The solution was mix with the transparent gelatin matrix before it become cooler, and grinded homogeneous thoroughly to obtain Mirabilitum Praeparatum cavum oris gelata after cooled.

Example 8: Mirabilitum Praeparatum Pelliculae Pro Cavo Oris

The polyvinyl alcohol and carboxymethylcellulose sodium was soaked with an appropriate amount of purified water for inflation and heated on water bath to dissolve, respectively. The both were mixed homogeneous for standby. An appropriate amount of Mirabilitum Praeparatum extract was dissolved with some hot purified water, added saccharin sodium and glycerol and stirred to dissolve. The solution was mixed with the standby polyvinyl alcohol and carboxymethylcellulose sodium mixture, added an appropriate amount of purified water to required amount and mix homogeneous, and then stranded for depleting the bubble to paint film. The film was dried, defilming and cut into required size. The film was exposure to ultraviolet lamp for sterilization and then tight packed to obtain the Mirabilitum Praeparatum pelliculae pro cavo oris.

Example 9: Mirabilitum Praeparatum Buccal Tablets 65 g Mirabilitum Praeparatum extract was mixed with 70 g glucose, 75 g sucrose, and 75 g starch homogeneously and granulated with 95% ethanol, dried and tableting to obtain Mirabilitum Praeparatum buccal tablets.

Example 10: Mirabilitum Praeparatum Toothpaste Cosmetics 5 g Mirabilitum Praeparatum extract was mixed with weighted silicic acid hydrate, glycerol, sodium lauryl sulfonate, carboxymethylcellulose sodium, spice, and sweetening agent homogeneously and put into paste making machine for grinding thoroughly to obtain 100 g toothpaste. The toothpaste was used for preventing and nursing cavum oris ulcer, paradentosis, and gingivitis.

Example 11: The Clinical Observation of Mirabilitum Praeparatum Cavum Oris Gelata—Treatment on Cavum Oris Ulcer Drug: Mirabilitum Praeparatum cavum oris gelata
Patients: 50 outpatients, including 28 cases of man and 22 cases of women, aged from 18 to 62. The patients with endogenous diseases were excluded.

Medication: An appropriate amount of Mirabilitum Praeparatum cavum oris gelata was spread on par aff., 4~6 times a day for 5 d.

Criteria of evaluating curative effects: 1) Excellence: pain disappeared, the cavum oris ulcer healed. 2) Effective: pain alleviated, the cavum oris ulcer area decreased, swollen reduced, and unhealed. 3) Ineffective: pain unalleviated or aggravated, and cavum oris ulcer unimproved.

The result: the total effective rate was 94.2%, no adverse reaction.

The cavum oris ulcer, belongs to "kou chuang" in Chinese medical, which caused by surfeit pungent, accumulation of heart and spleen, and catching pathogens of wind, heating, and dryness. The Mirabilitum Praeparatum possesses the potencies of clearing away heat and reducing fire and reduces swelling and alleviates pain. The effect of Mirabilitum Praeparatum on cavum oris ulcer was significantly but no adverse reaction, and convenient in medication.

Example 12: The Clinical Observation of Mirabilitum Praeparatum Cavum Oris Gelata—Treatment on Acute and Chronic Pharyngolaryngitis Drug: Mirabilitum Praeparatum cavum extract.
Patients: 43 outpatients, including 23 cases of man and 20 cases of women, aged from 18 to 57. The patients with endogenous diseases were excluded.

Medication: An appropriate amount of Mirabilitum Praeparatum extract was administered under tongue, 2~5 times a day for 7d.

Criteria of evaluating curative effects: 1) Clinical cured: all symptoms of sore throat and cough disappeared after administrated for less than 7d. 2) Excellence: most symptoms of sore throat and cough disappeared after administrated for less than 7d. 3) Effective: symptoms of sore throat and cough reduced for more than 50% after administrated for less than 7d. Ineffective: symptoms of sore throat and cough reduced for less than 50% or aggravated after administrated for less than 7d.

The result: the total effective rate was 92.25%, no adverse reaction.

Example 13: The Clinical Observation of Mirabilitum Praeparatum Cavum Oris Gelata—Treatment on Tonsillitis Drug: Mirabilitum Praeparatum buccal tablets.
Patients: 60 outpatients, including 28 cases of man and 32 cases of women, aged from 18 to 57. The patients with endogenous diseases were excluded.

Medication: Mirabilitum Praeparatum buccal tablets, 3~5 tablets a day for 7d.

Criteria of evaluating curative effects (bacteriology criteria): 1) Clearance: all pathogenic bacteria disappeared and no other pathogenic bacteria appeared after administrated for 7d. 2) Unclearance: the pathogenic bacteria unchanged after administrated for 7d. 3) Bacterial replacement: all pathogenic bacteria were cleared and other pathogenic bacteria appeared but no infection after administrated for 7d, and not need to be treated.

The result: the bacterial clearance was up to 87.8% and the total effective rate was 92.25%, no adverse reaction.

The Examples described above were the optimizations of the present invention. It should be pointed out that the invention could be improved and polished on the basis of the present materials by common technicians of this field, but the improvements and polishes of the present invention should also be contained in protection domain.

The invention claimed is:

1. A method for preparation of Mirabilitum Praeparatum by pure strain fermentation, comprising:
    mixing ripe fruit (watermelon) of *Citrullus Ianatus* (Thunb.) Matsum. et Nakai and mirabilitum (Na$_2$SO$_4$·10H$_2$O) according to a ratio of 100:50-100:1 (watermelon/mirabilitum, by weight) to form a mixture; and
    adding *Penicillium rubens* as a zymophyte to the mixture and fermenting the mixture to obtain the Mirabilitum Praeparatum.

2. A method for preparation of Mirabilitum Praeparatum by pure strain fermentation, comprising:
    cutting fresh ripe fruit (watermelon) of *Citrullus Ianatus* (Thunb.) Matsum. et Nakai into small pieces and putting the small pieces into a fermenter;
    adding to the fermenter mirabilitum according to a ratio of 100:50-100:1 (watermelon/mirabilitum, by weight);
    mixing the fruit and mirabilitum until a resulting mixture is homogeneous;
    sterilizing the mixture with high-pressure (15 psi) steam for 20 minutes at 121° C.;
    inoculating *Penicillium rubens* to ferment for at least 15 days at 19-27° C.;
    dissolving oxygen during fermentation;
    centrifuging the mixture for 10-20 minutes at 4000 r/minute to form a supernate; and
    drying the supernate with a freezer dryer (−40° C., <13 Pa) to obtain the Mirabilitum Praeparatum.

3. The method of claim 2, wherein a ratio of the ripe fruit (watermelon) of *Citrullus Ianatus* (Thunb.) Matsum. et Nakai and Mirabilitum Citrulli Preparatum by weight is 20:3.

4. The method of claim 2, wherein the inoculating operation is carried out at 25° C.

5. The method of claim 2, wherein the inoculating operation is carried out for 15-35 days.

* * * * *

SEQUENCE LISTING

<160> NUMBER OF SEQ ID NOS: 1

<210> SEQ ID NO 1
<211> LENGTH: 566
<212> TYPE: DNA
<213> ORGANISM: Mirabilitum praeparatum

<400> SEQUENCE: 1

```
aagtcgtaac aaggtttccg taggtgaacc tgcggaagga tcattaccga gtgagggccc      60
tctgggtcca acctcccacc cgtgtttatt ttaccttgtt gcttcggcgg gcccgcctta     120
actggccgcc gggggcgctta cgcccccggg cccgcgcccg ccgaagacac cctcgaactc     180
tgtctgaaga ttgtagtctg agtgaaaata taaattattt aaaactttca acaacggatc     240
tcttggttcc ggcatcgatg aagaacgcag cgaaatgcga tacgtaatgt gaattgcaaa     300
ttcagtgaat catcgagtct ttgaacgcac attgcgcccc ctggtattcc gggggcatg      360 cctgtccgag cgtcatttct gccctcaagc acggcttgtg tgttgggccc cgtcctccga     420
tcccggggga cgggcccgaa aggcagcggc ggcaccgcgt ccggtcctcg agcgtatggg     480
gctttgtcac ccgctctgta ggcccggccg gcgcttgccg atcaacccaa atttttatcc     540
aggttgacct cggatcaggt agggta                                          566
```